(12) United States Patent
Whittle et al.

(10) Patent No.: US 8,034,843 B2
(45) Date of Patent: Oct. 11, 2011

(54) COMPOSITIONS COMPRISING CANNABINOIDS FOR TREATMENT OF NAUSEA, VOMITING, EMESIS, MOTION SICKNESS OR LIKE CONDITIONS

(75) Inventors: Brian Whittle, Hornsea (GB); Farideh Afshin Javid, Yorkshire (GB)

(73) Assignee: GW Pharma Limited, Salisbury, Wiltshire (GB)

( * ) Notice: Subject to any disclaimer, the term of this patent is extended or adjusted under 35 U.S.C. 154(b) by 566 days.

(21) Appl. No.: 10/502,822

(22) PCT Filed: Feb. 3, 2003

(86) PCT No.: PCT/GB03/00451
§ 371 (c)(1),
(2), (4) Date: Mar. 2, 2005

(87) PCT Pub. No.: WO03/063847
PCT Pub. Date: Aug. 7, 2003

(65) Prior Publication Data
US 2005/0165088 A1 Jul. 28, 2005

(30) Foreign Application Priority Data

Feb. 1, 2002 (GB) .................................. 0202385.1
Mar. 15, 2002 (GB) .................................. 0206183.6

(51) Int. Cl.
*A01N 37/10* (2006.01)
*A01N 65/00* (2009.01)
*A61K 31/19* (2006.01)
*A61K 36/00* (2006.01)

(52) U.S. Cl. ........................................ 514/568; 424/774
(58) Field of Classification Search .................. 514/568; 424/774
See application file for complete search history.

(56) References Cited

U.S. PATENT DOCUMENTS

| | | | |
|---|---|---|---|
| 4,847,290 A | 7/1989 | Burstein | |
| 5,434,295 A | 7/1995 | Mechoulam et al. | |
| 5,874,459 A * | 2/1999 | Makriyannis et al. | ........ 514/425 |
| 6,113,940 A | 9/2000 | Brooke et al. | |
| 6,162,829 A | 12/2000 | Burstein | |
| 6,328,992 B1 * | 12/2001 | Brooke et al. | ................ 424/449 |
| 6,383,513 B1 | 5/2002 | Watts et al. | |
| 6,403,126 B1 * | 6/2002 | Webster et al. | ............... 424/776 |

FOREIGN PATENT DOCUMENTS

| | | |
|---|---|---|
| GB | 2386322 A | 9/2003 |
| WO | WO 93/05031 A1 | 3/1993 |
| WO | WO 99/52524 A1 | 10/1999 |
| WO | WO 01/03668 A1 | 1/2001 |
| WO | WO 01/95899 A2 | 12/2001 |
| WO | WO 01-98289 A1 | 12/2001 |
| WO | WO 02/32420 A1 | 4/2002 |
| WO | WO 02-064109 A2 | 8/2002 |
| WO | WO 02/069993 A1 | 9/2002 |
| WO | WO 03/037306 A2 | 5/2003 |

OTHER PUBLICATIONS

El-Darawy et al. (1972) Studies on Hashish, Isolation & Identification of Cannabinols and Effect of Certain Factors. Qual. Plant. Mater. Veg. XX1, 4, pp. 311-325.*
Baek et al. (1985) Boron Trifluoride Etherate on Alimina. A Modified Lewis Acid Reagent. An Improved Synthesis of Cannabidiol. Tetrahedron Letters. vol. 26, No. 8, pp. 1083-1086.*
Watanabe et al. Biol. Pharm. Bull. Aug. 1996, vol. 19, No. 8, pp. 1109-1111.*
Koch, KL. Illusory self-motion and motion sickness: a model for grain-gut interaction and nausea. DigDIS Sci. Aug. 1999, vol. 44, 8 Suppl. pp. 53S-57S, abstract submitted only.*
The United Kingdom Parliament, Select Committee on Science and Technology Ninth Report (1998) at http://www.parliament.the-stationery-office.co.uk/pa/Id199798/Idselect/Idsctech/151/15101.htm.
The United Kingdom Parliament, Select Committee on Science and Technology Second Report (Mar. 14, 2001) at http://www.publications.parliament.uk/pa/Id200001/Idselect/Idsctech/50/5001.htm.
Darmani, N.A., "The potent emetogenic effects of the endocannabinoid, 2-AG (2-Arachidonoylglycerol) are blocked by $\Delta^9$-tetrahydrocannabinol and other cannabinoids," *The Journal of Pharmacology and Experimental Therapeutics* 2002; 300(1):34-42.
"Cannabinoid" at http://en.wikipedia.org/wiki/Cannabinoid, downloaded on Aug. 10, 2009 from Wikipedia, the free encyclopedia (12 pages).
Adams, R. et al., "Structure of Cannabidiol. XII. Isomerization to Tetrahydrocannabinols," *Journal of the American Chemical Society* 1941; 63:2209-2213.
BIOSIS Abstract Acct. No. PREV200200002690 of Society for Neuroscience Abstracts, vol. 27, No. 2, Nov. 2002, Darmani, N.A., "The endogenous cannabinoid 2-arachidonoylglycerol induces vomiting: Blockade by marijuana and its synthetic analogs," p. 2126.
Burstein, S.H. "The cannabinoid acids: Nonpsychoactive derivatives with therapeutic potential," *Pharmacology and Therapeutics* 1999; 82(1):87-96.
Medline Abstract Acc. No. NLM11752094 of the Journal of Pharmacology and Experimental Therapeutics, vol. 300, No. 1, Jan. 2002, Darmani, N.A., "The potent emetogenic effects of the endocannabinoid, 2-AG (2-arachidonoylglycerol) are blocked by delta(9)-tetrahydrocannabinol and other cannabinoids," pp. 34-42.
Molnar, J. et al., "Membrane associated antitumor effects of crocine-ginsenoside- and cannabinoid derivatives," *Anticancer Research* Mar. 2000; 20(2A):861-868.
Parker, L. et al., "Cannabidiol, a non-psychoactive component of cannabis and its synthetic dimethylheptyl homolog suppress nausea in an experimental model with rats," *Neuroreport*. Apr. 16, 2002; 13(5):567-570.
Yamamoto, I. et al., "Recent advances in the metabolism of cannabinoids," *International Journal of Biochemistry and Cell Biology* 1995; 27(8):741-746.
Yotoriyama, M. et al., "Comparison of pharmacological activity in mice of different cannabis extracts from CBDA and THCA strains," *Esei Kagaku* 1991; 37(6):507-511.

* cited by examiner

*Primary Examiner* — Sreeni Padmanabhan
*Assistant Examiner* — Samira Jean-Louis
(74) *Attorney, Agent, or Firm* — Wolf, Greenfield & Sacks, P.C.

(57) ABSTRACT

Cannabinoids, in particular CBD and CBDA and their acid derivatives are provided for use as an active pharmaceutical substance in the treatment of nausea, vomiting, emesis, motion sickness. In particular extracts of cannabis plants are presented which are rich in these substances and suitable for pharmaceutical use.

16 Claims, 5 Drawing Sheets

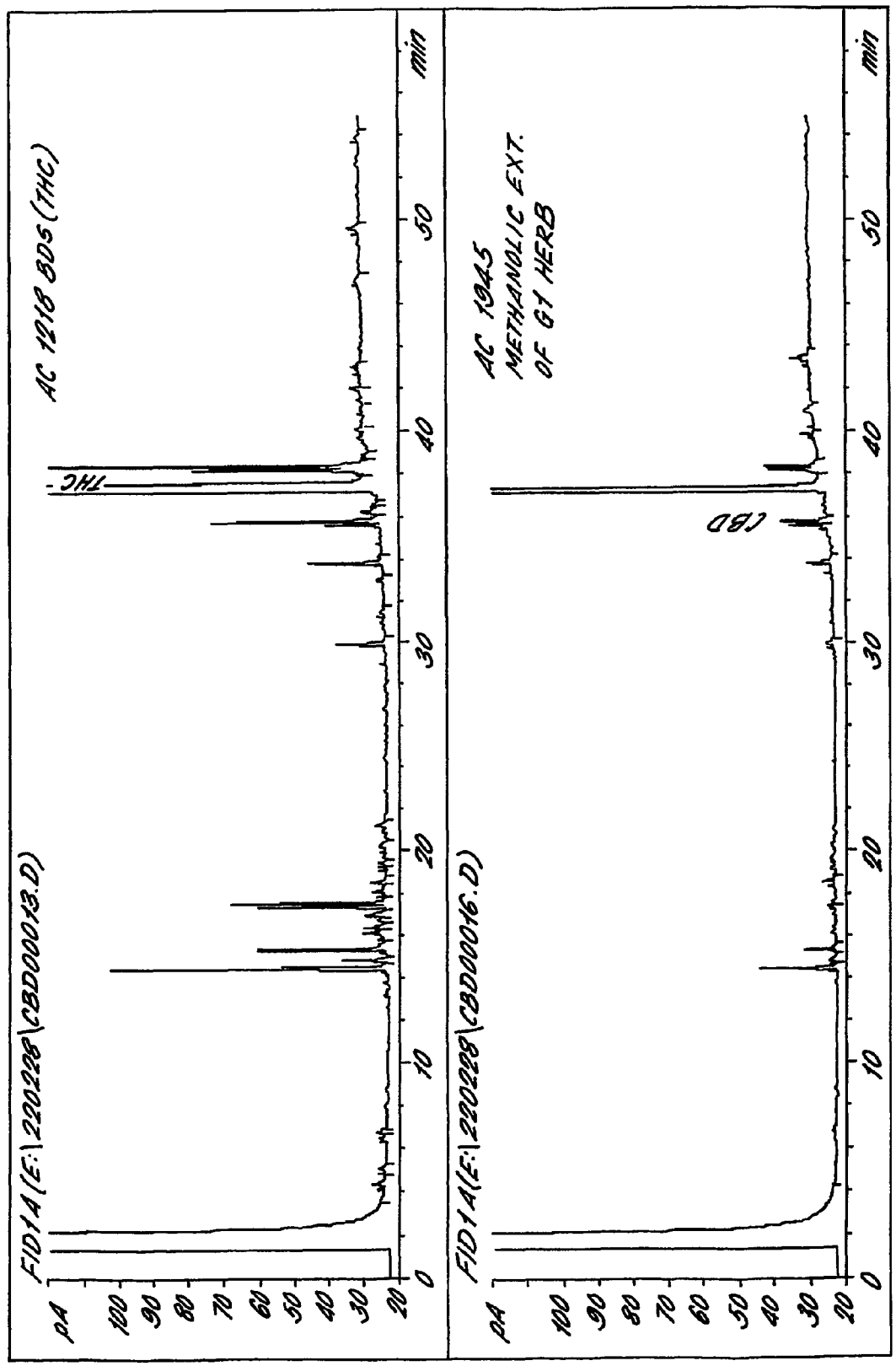

COMPOSITIONS COMPRISING CANNABINOIDS FOR TREATMENT OF NAUSEA, VOMITING, EMESIS, MOTION SICKNESS OR LIKE CONDITIONS

RELATED APPLICATIONS

This application is a national stage filing under 35 U.S.C. §371 of PCT International application PCT/GB2003/000451, filed Feb. 3, 2003, which was published under PCT Article 21(2) in English.

Functional vomiting is the forceful expulsion of gastric contents produced by involuntary contraction of the abdominal musculature. This occurs when the gastric fundus and lower oesophageal sphincter are relaxed. Functional vomiting may be accompanied by nausea (an unpleasant feeling that vomiting is about to occur). Nausea is associated with altered physiological activity, including gastric hypomotility, and increased parasympathetic tone. Nausea may precede and accompany vomiting. They represent the patient's awareness of afferent stimuli to the medullary vomiting centre.

Physiological vomiting is a functional condition that occurs in response to a number of factors affecting the vomiting centre. It may also be triggered by peripheral factors such as ingestion of toxins, disturbance of the vestibular system, peritoneal inflammation and bowel obstruction. It may also occur in disorders of delayed gastric emptying as, for example, in diabetes and idiopathic gastroparesis.

Psychogenic vomiting may be self-induced or may occur involuntarily in situations that are anxiety inducing, threatening or in some way regarded as distasteful by the subject. It is also possible that psychological factors leading to vomiting are culturally determined (for example, eating exotic food may be considered repulsive in the subject's own cultural group). Vomiting may also express hostility as when children vomit during a temper tantrum or in certain conversion disorders.

Nausea and vomiting may also be induced by cytotoxic chemotherapy and radiotherapy. Post-operatively, patients may also vomit and experience nausea, which may be attributable to the anaesthetic and analgesic agents frequently administered concurrently.

There are therefore peripheral and central mechanisms which are involved in the expression of nausea and frank vomiting. Existing therapies are available for the treatment of these conditions but they have limitations, and there is a need for alternative treatments, particularly where these can exert their effect through a central nervous mechanism.

Investigation of a number of agents in a conscious animal model in which motion sickness is induced has confirmed that extracts of cannabis have an anti-emetic effect. Conventionally, the anti-emetic effect of cannabis has been ascribed to delta$^9$-tetrahydrocannabinol ($\Delta^9$-THC). The use of a whole animal, conscious model to explore this effect, and the availability of cannabis extracts containing predominantly one cannabinoid or another have allowed for more detailed analysis of the contribution of specific cannabinoids.

Surprisingly, it has been found that the anti-emetic effect, in a model of motion sickness in *Suncus murinus* (the Asian musk (house) shrew), is greatest in high cannabidiol (CBD) (and/or its acid form CBDA) containing extracts rather than in high tetrahydrocannabinol (THC) (and/or its acid form THCA) containing extracts (greater than 50% CBD more preferably greater than 80% most preferably greater than 90% relative to other cannabinoids present).

It is hypothesised that the results will extend to the propyl variant of CBD, namely CBDV and its acid form CBDVA.

More particularly, the results were noted in extracts in which the cannabinoids were predominantly in their acid form since the extracts were prepared by a methanolic extraction and had not been subjected to a decarboxylation step by, for example, heating. It is possible therefore that the therapeutic effects noted are due to the acid form of the cannabinoids. If it is the acid form of the cannabinoid that is responsible for the observed therapeutic effect this is particularly surprising since the acid forms of cannabinoids have not hitherto been known to exhibit therapeutic effects.

According to a first aspect of the present invention there is provided a cannabis extract, rich in CBD and/or CBDA and/or the propyl variants CBDV and/or CBDVA, for use in the manufacture of a medicament for the treatment of nausea, vomiting, emesis, motion sickness or like conditions.

By rich is meant greater than 2% w/w of CBD and/or CBDA and/or the propyl variants CBDV and/or CBDVA, more particularly greater than 5%, more preferably still greater than 7%.

According to another aspect of the present invention there is provided the use of CBD and/or CBDV in the manufacture of a medicament for the treatment of nausea, vomiting, emesis, motion sickness or like conditions.

According to another aspect of the present invention there is provided a cannabinoid acid for use as an active pharmaceutical substance.

According to yet another aspect of the present invention there is provided CBDA or CBDVA for use as an active pharmaceutical substance.

Preferably the active pharmaceutical substance is present as a medicament for the treatment of nausea, vomiting, emesis, motion sickness or like conditions.

In one embodiment the CBD and/or CBDA and/or CBDV and/or CBDVA are present with other cannabinoids as a mixture derived from a plant extract (CMBE, cannabis based medicinal extract).

Plant extracts are preferred as, in addition to one or more cannabinoids, they will contain other chemical entities that may provide a beneficial effect either in their own right or in combination with the one or more cannabinoids. Such other chemicals include, for example, volatile oils e.g. terpene or carotene rich volatiles. Known terpenes present in the CMBE include $C_{10}$ terpenes, e.g. mycerene, and pinenes and $C_{15}$ terpenes e.g. caryophyllene.

Preferably the CBD or CBDV and/or the acids thereof are present with THC or THCV and/or the acids thereof.

Alternatively the CBD or CBDV and/or the acids thereof are substantially free (less than 10%, more prferably less than 5% and most preferably less than 2% relative to other cannabinoids present) from other cannabinoids.

In another embodiment the CBD or CBDV and/or the acids thereof are synthetic.

The invention also extends to methods of treating nausea, vomiting, emesis, motion sickness or like conditions with CBD or CBDV and/or the acids thereof, either as the sole active ingredient or in mixtures as plant extracts.

Whilst the observation has been made on an extract administered intraperitoneally, the skilled man will appreciate that a medicament can be prepared for administration by any suitable means. These include, but are not limited to, solids, semi solids, e.g. gels, liquids, sprays, aerosols, inhalers, vapourisers, enemas, rectal suppositories and the like. The route of administration need not be intraperitoneally but could be oral, buccal, sublingual, or by any other suitable route e.g. the respiratory tract, nasal tract and distal rectum.

A "plant extract" is an extract from a plant material as defined in the Guidance for Industry Botanical Drug Products Draft Guidance, August 2000, US Department of Health and Human Services, Food and Drug Administration Centre for Drug Evaluation and Research.

"Plant material" is defined as a plant or plant part (e.g. bark, wood, leaves, stems, roots, flowers, fruits, seeds, berries or parts thereof) as well as exudates.

The term "*Cannabis* plant(s)" encompasses wild type *Cannabis* sativa and also variants thereof, including *cannabis chemovars* which naturally contain different amounts of the individual cannabinoids, *Cannabis sativa* subspecies *indica* including the variants var. *indica* and var. *kafiristanica*, *Cannabis indica* and also plants which are the result of genetic crosses, self-crosses or hybrids thereof. The term "*Cannabis* plant material" is to be interpreted accordingly as encompassing plant material derived from one or more *cannabis* plants. For the avoidance of doubt it is hereby stated that "*cannabis* plant material" includes dried *cannabis* biomass.

In the context of this application the terms "cannabis extract" or "extract from a *cannabis* plant", which are used interchangeably encompass "Botanical Drug Substances (BDS)" derived from *cannabis* plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes." A botanical drug substance does not include a highly purified or chemically modified substance derived from natural sources. Thus, in the case of *cannabis*, "botanical drug substances" derived from *cannabis* plants do not include highly purified, Pharmacopoeial grade cannabinoids.

"Botanical drug substances" derived from *cannabis* plants include primary extracts prepared by such processes as, for example, maceration, percolation, extraction with solvents such as C1 to C5 alcohols (e.g. ethanol), Norflurane (HFA134a), HFA227 and liquid carbon dioxide under pressure. The primary extract may be further purified for example by supercritical or subcritical extraction, vaporisation and chromatography. When solvents such as those listed above are used, the resultant extract contains non-specific lipid-soluble material. This can be removed by a variety of processes including "winterisation", which involves chilling to $-20°$ C. followed by filtration to remove waxy ballast, extraction with liquid carbon dioxide and by distillation.

Preferred "*cannabis* extracts" include those which are obtainable by using any of the methods or processes specifically disclosed herein for preparing extracts from *cannabis* plant material. The extracts are preferably substantially free of waxes and other non-specific lipid soluble material but preferably contain substantially all of the cannabinoids naturally present in the plant, most preferably in substantially the same ratios in which they occur in the intact *cannabis* plant.

Botanical drug substances are formulated into "Botanical Drug Products" which are defined in the Guidance for Industry Botanical Drug Products Draft Guidance, August 2000, US Department of Health and Human Services, Food and Drug Administration Centre for Drug Evaluation and Research as: "A botanical product that is intended for use as a drug; a drug product that is prepared from a botanical drug substance."

"Cannabinoids" may be highly purified, Pharmacopoeial Grade substances and may be obtained by purification from a natural source or via synthetic means. The cannabinoids will include, but are not limited to, tetrahydrocannabinoids, their precursors, alkyl (particularly propyl) analogues, cannabidiols, their precursors, alkyl (particularly propyl) analogues, and cannabinol.

In preferred embodiments of the invention the formulations comprise extracts of one or more varieties of whole *Cannabis* plants, particularly *Cannabis sativa*, *Cannabis indica* or plants which are the result of genetic crosses, self-crosses or hybrids thereof. The precise cannabinoid content of any particular *cannabis* variety may be qualitatively and quantitatively determined using methods well known to those skilled in the art, such as TLC or HPLC. Thus, one may chose a *Cannabis* variety from which to prepare an extract which will produce the desired ratio of CBD or CBDV to THC or THCV. Alternatively, extracts from two of more different varieties may be mixed or blended to produce a material with the preferred cannabinoid ratio for formulating into a pharmaceutical formulation.

The preparation of convenient ratios of CBD, CBDV, CBDA and CBDVA-containing medicines is made possible by the cultivation of specific chemovars of *cannabis*. These chemovars (plants distinguished by the cannabinoids produced, rather than the morphological characteristics of the plant) can be bred by a variety of plant breeding techniques which will be familiar to a person skilled in the art. Suitable methods are given in Example 3. Propagation of the plants by cuttings for production material ensures that the genotype is fixed and that each crop of plants contains the cannabinoids in substantially the same ratio.

Horticulturally, it is convenient to grow chemovars producing e.g. CBD and CBDV as the predominant cannabinoid from cuttings. This ensures that the genotype in each crop is identical and the qualitative formulation (the proportion of each cannabinoid in the biomass) is the same. From these chemovars, extracts can be prepared by the similar method of extraction. Convenient methods of preparing primary extracts include maceration, percolation, extraction with solvents such as C1 to C5 alcohols (ethanol), Norflurane (HFA134a), HFA227 and liquid carbon dioxide under pressure. The primary extract may be further purified for example by supercritical or subcritical extraction, vaporisation and chromatography. When solvents such as those listed above are used, the resultant extract contains non-specific lipid-soluble material. This can be removed by a variety of processes including chilling to $-20°$ C. followed by filtration to remove waxy ballast, extraction with liquid carbon dioxide and by distillation. Preferred plant cultivation and extract preparation methods are shown in the Examples. The resulting extract is suitable for incorporation into pharmaceutical preparations.

A detailed examination of the pharmacological differences between CBD and THC has revealed significant differences in these compounds and consequently the finding that CBD and/or its acid CBDA appear to be responsible for the therapeutic effects noted was surprising. THC is bound with high avidity to CB1 and CB2 receptors in cerebral cortex and other sites; CBD is relatively inactive against CB1 receptors and appears to have non-cannabinoid receptor pharmacological actions in the central nervous system. Without prejudice to the teaching of the invention, it is possible that the anti-emetic effect of CBD and/or its acid CBDA is mediated via a non-cannabinergic mechanism.

Table 1 below illustrates some of the differences between these cannabinoids.

TABLE 1

| Effect | THC | THCV | CBD | CBDV | Reference |
|---|---|---|---|---|---|
| $CB_1$ (Brain receptors) | ++ |  | ± |  | Pertwee et al, 1998 |
| $CB_2$ (Peripheral receptors) | + |  | − |  |  |
| CNS Effects |  |  |  |  |  |
| Anticonvulsant † | −− |  | ++ |  | Carlini et al, 1973 |
| Antimetrazol | − |  | − |  | GW Data |
| Anti-electroshock | − |  | ++ |  | GW data |
| Muscle Relaxant | −− |  | ++ |  | Petro, 1980 |
| Antinociceptive | ++ |  | + |  | GW data |
| Catalepsy | ++ |  | ++ |  | GW data |
| Psychoactive | ++ |  | − |  | GW data |
| Antipsychotic | − |  | ++ |  | Zuardi et al, 1991 |
| Neuroprotective antioxidant activity* | + |  | ++ |  | Hampson A J et al, 1998 |
| Antiemetic | ++ |  | − |  |  |
| Sedation (reduced spontaneous activity) | + |  | + |  | Zuardi et al, 1991 |
| Appetite stimulation | ++ |  |  |  |  |
| Appetite suppression |  |  | ++ |  |  |
| Anxiolytic | − |  | ++ |  | GW data |
| Cardiovascular Effects |  |  |  |  |  |
| Bradycardia | − |  | + |  | Smiley et al, 1976 |
| Tachycardia | + |  | − |  |  |
| Hypertension § | + |  | − |  |  |
| Hypotension § | − |  | + |  | Adams et al, 1977 |
| Anti-inflammatory Immunomodulatory/antiinflammatory activity | ± |  | ± |  | Brown, 1998 |
| Raw Paw Oedema Test | − |  | ++ |  | GW data |
| Cox 1 |  |  |  |  | GW data |
| Cox 2 |  |  |  |  | GW data |
| TNFα Antagonism | + | + | ++ | ++ |  |
| Glaucoma | ++ |  | + |  |  |

*Effect is CB1 receptor independent.
† THC is pro convulsant
§ THC has a biphasic effect on blood pressure; in naïve patients it may produce postural hypotension and it has also been reported to produce hypertension on prolonged usage. GW Internal Report No 002/000159.

Whilst it is known that THC can be used to control nausea and vomiting pre-operatively the effect of other cannabinoids or combinations or the effect of the acid forms present in, for example, plant extracts was not hitherto known.

The applicants studied the effect of other cannabinoids as cannabis extracts, and particularly extracts containing predominantly CBD or its acid form CBDA in *Suncus murinus* and in which an emetic response can be induced by a motion stimulus. Compounds which are effective in this test have therapeutic benefit in the treatment of motion-induced nausea and vomiting, and also these conditions when induced by other pathways in the peripheral and central nervous systems.

The applicant has determined that, for example, extracts in which the content of CBD and/or CBDA is 2-20% w/w, and the content of THC and or THCA is 0.1-2% w/w are particularly beneficial.

The invention is further illustrated with reference to the accompanying figures and examples:

FIG. 1 is a TLC from the methanolic extract of the high CBD chemovar G5 (M16). It shows significant CBD and CBDA peaks at around 6 and 7 minutes and lesser amounts of THC and THCA at around 10 and 18 minutes.

FIG. 2 is the TLC the methanolic extract of the high THC chemovar G2 (M6). It shows significant THC and THCA peaks at around 10 and 18 minutes along with lesser amounts of CBD and CBDA at around 6 and 7 minutes.

The figures shown in FIGS. 1 and 2 are quantitative.

FIG. 5 illustrates the results obtained for G2, the upper trace being for the BDS (decarboxylated and extracted by sub critical liquid $CO_2$) and the lower trace for the methanolic extract. The CBD peak at 35 minutes and the THC peak at 37 minutes are marked.

EXAMPLE 1

Extracts of *cannabis* can be prepared by a number of solvent extraction techniques, including the use of organic solvents alone or in admixture with water and under sub critical or supercritical conditions. Cannabinoids may be present in *cannabis* biomass as free cannabinoids and as the corresponding acidic precursors. Conventional methods of preparation involve the total extraction of free cannabinoids and precursors with solvents such as lower alkyl alcohols, particularly methanol. In this example, total extracts of a high THC, and a high CBD-containing chemovar were made using methanol.

Biomass from each chemovar was separately extracted in a column with methanol at room temperature, and the pooled percolate was collected. Solvent was removed by evaporation in a rotary evaporator at a temperature not exceeding 43° C. The resulting high THC and high CBD extracts were dispersed in 5% Polysorbate 80/normal saline and a Polysorbate/saline vehicle was used as control. The high THC extract (M6) contained more than 10% of THC and/or THCA and less than 1% of CBD and/or CBDA. The high CBD extract (M16) contained more than 7.3% of CBD and/or CBDA and less than 2% of THC and/or THCA.

A preliminary HPLC analysis of the methanolic extracts (and comparative data for a botanical drug substance (BDS), when prepared by sub critical $CO_2$ extraction after decarboxylation) is given in the table 2 below:

TABLE 2

| Extract/Analyte | Methanolic extract from a CBD rich chemovar % w/w | Comparative Decarboxylated $CO_2$ extract from THC rich chemovar % w/w | Comparative Decarboxylated $CO_2$ extract from CBD rich chemovar % w/w |
|---|---|---|---|
| THC | N.D. | 64.2% | 2.9% |
| THCA | 1.4% | N.D. | N.D. |
| CBD | 6.1% | 1.1% | 70.2% |
| CBDA | 49.9% | N.D. | N.D |
| CBN | N.D. | 1.0% | N.D. |

As would be expected, the acid forms of the cannabinoid predominate in the methanolic extract of the non-decarboxylated herb.

For the methanolic extracts the % w/w of the principal cannabinoid (sum of acid+neutral forms) is lower than found in the equivalent BDS. Again, this is to be expected due to the lower selectivity of the methanol, as compared to liquid $CO_2$. Thus, the methanolic extraction gives rise to the extraction of more non-target material and a diluting of the active content of the extract.

Figure 1:
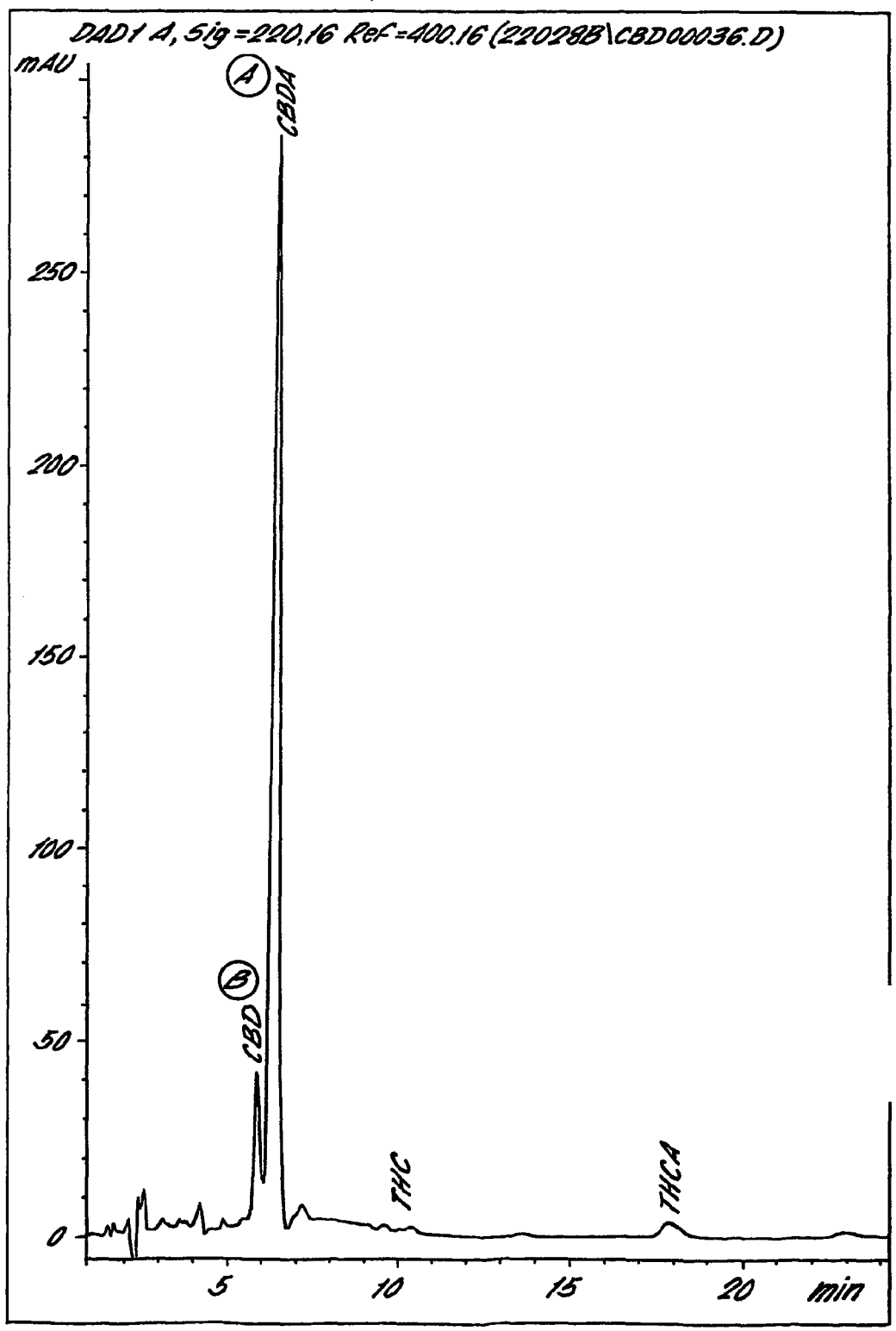
Figure 2:
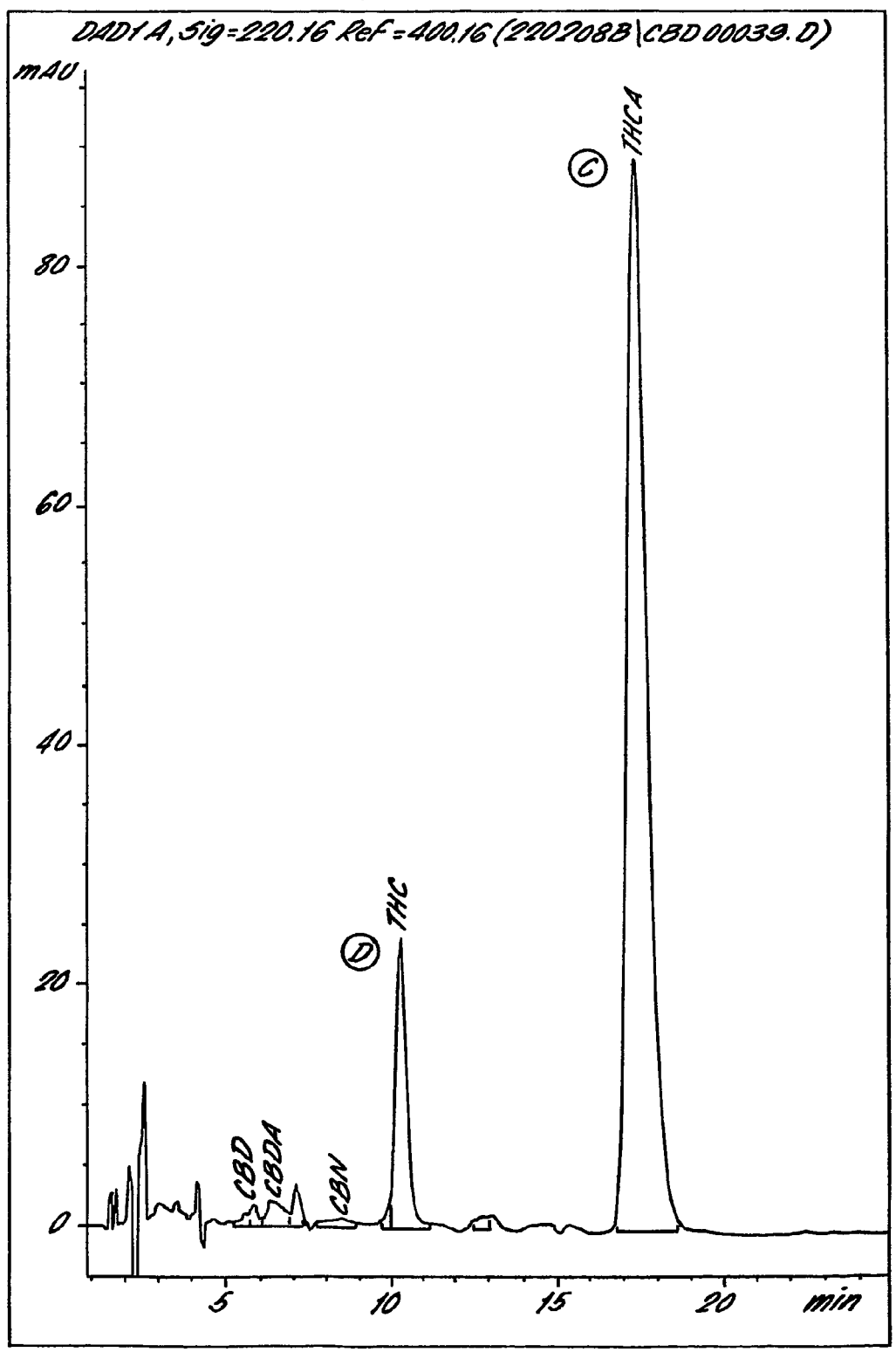

The content of the methanolic extract was confirmed by TLC analysis and chromatogram traces for the high THC and high CBD extracts are shown in FIGS. 1 and 2.

The traces in FIGS. 1 and 2 indicate the acid form of the cannabinoid to be the principal component observed, with smaller amounts of the corresponding neutral cannabinoid also being detected.

Figure 3:
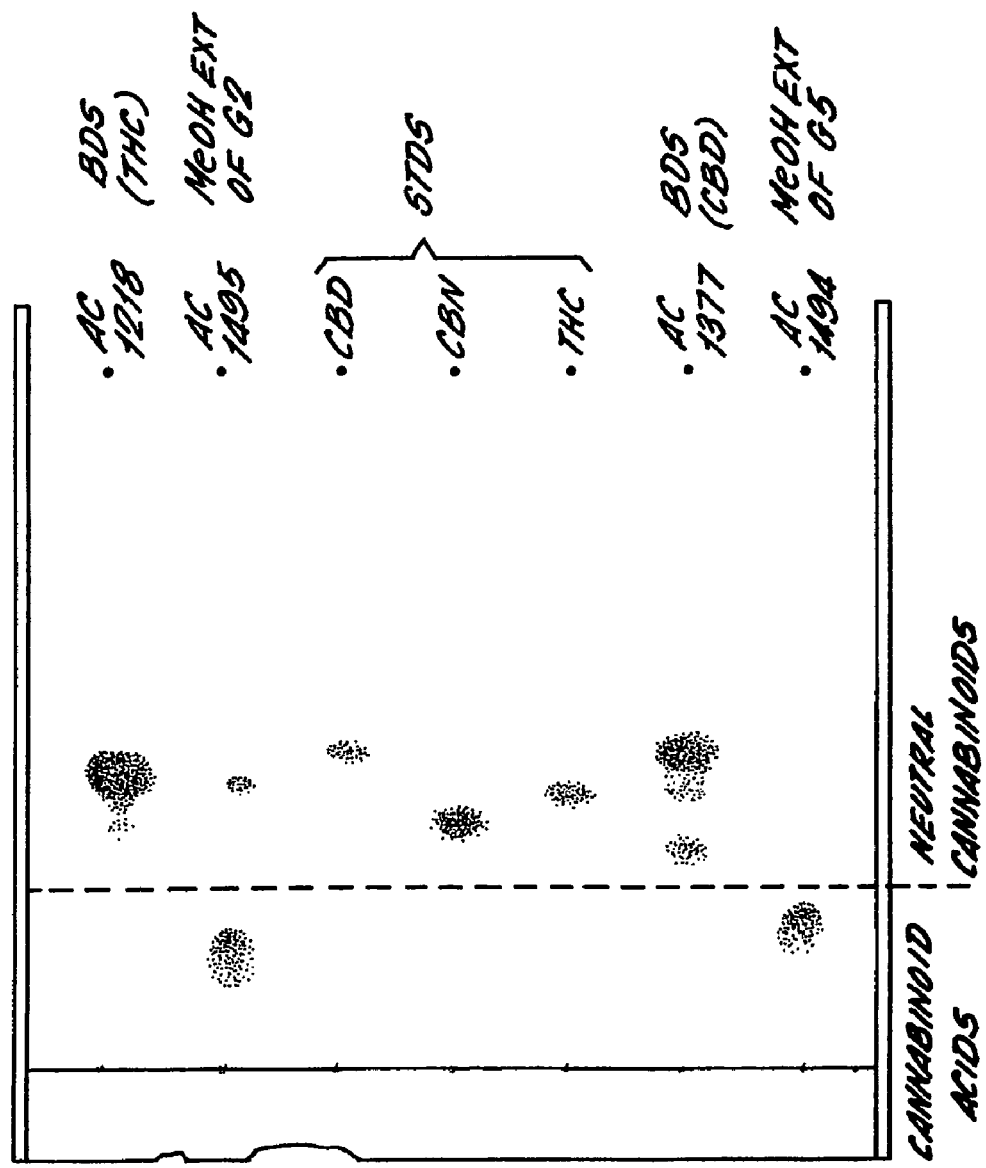
FIG. 3 is a thin layer chromatography plate showing the methanolic extracts, and by way of comparison BDS (decarboxylated and extracted by sub critical liquid $CO_2$). The results confirm that the methanolic extracts comprise a high proportion of the respective cannabinoids THC and CBD in what was later shown to be their acid forms.

Samples of the methanolic extracts were run on a TLC plate along with some cannabinoid markers, and by way of comparison botanic drug substance (BDS) (decarboxylated and extracted by sub critical liquid $CO_2$). The results are illustrated in FIG. 3.

Further analysis of the methanolic extracts, and by way of comparison the BDS (decarboxylated and extracted by sub critical liquid $CO_2$), using gas chromatography indicates the presence of terpenes at around the 14 to 18 minute mark. It should be noted that because G.C. is operated at around 250° C. any acid form of the CBD and THC present in the extracts will be decarboxylated and appear on the trace as CBD or THC. The results are illustrated in FIGS. 4 and 5.

Figure 4:
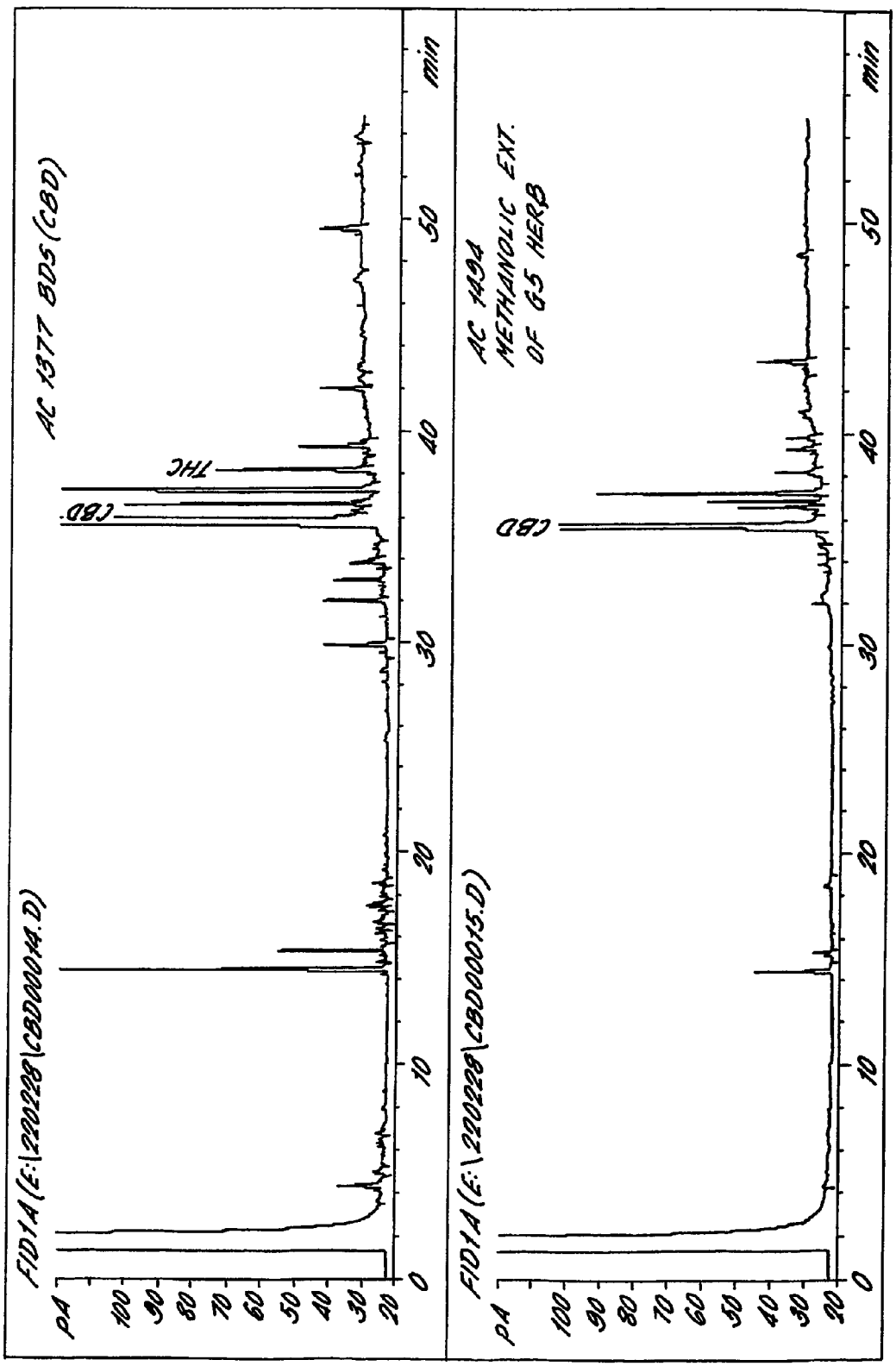
FIG. 4 illustrates the results obtained for G5, the upper trace being for the BDS (decarboxylated and extracted by sub critical liquid $CO_2$) and the lower trace for the methanolic extract. The CBD peak at 35 minutes and the THC peak at 38 minutes are marked.

The most significant difference between the lower traces of FIGS. 4 and 5 is the difference between the THC and CBD peaks.

EXAMPLE 2

Adult *Suncus murinus* (30-89 g bodyweight) of either sex were injected with either G2 (M6) or G5 (M16) at a range of doses from 1.0, 2.0 or 4.0 mg/kg (or vehicle), intraperitoneally, 30 minutes prior to a motion stimulus (1 Hz 40 mm amplitude of shaking for 10 minutes). The animals were observed for any overt behavioural change. A number of emetic episodes and the latency of onset were recorded. Data were expressed as the mean±s.e.m., group size n=6 and statistically analysed using ANOVA, followed by Bonferronni Dunnett's T test. The results are summarised in table 3 below.

TABLE 3

Effect of Cannabis Extracts given Intraperitoneally on Frequency of Latency to First Emesis (means ± s.e.m.)

| Treatment | Dose mg/kg | Latency (secs) | P value | Number | P Value |
|---|---|---|---|---|---|
| Vehicle control | | 103.0 + 25.3 | | 12.4 + 2.4 | |
| M16 | 1.0 | 206.8 ± 33.9 | <0.05 | 6.3 ± 1.4 | <0.05 |
| High CBD | 2.0 | 250.5 ± 84.5 | <0.05 | 6.6 ± 2.4 | <0.05 |
| chemovar | 4.0 | Increase | N5 | Increase | N5 |
| M6 | 1.0 | † NDDC | | NDDC | |
| High THC | 2.0 | NDDC | | NDDC | |
| chemovar | 4.0* | <100 | | >18 | <0.05 |

† NDDC no detectable difference from control
*Increase in vomiting, reduction in latency The results for the high CBD producing chemovar extract (M16) shown in Table 3 are not unlike U-shaped dose response curves noted for some other pharmacological actions of cannabinoids.

The lack of effect of the high THC producing chemovar extract in this test system is surprising. Indeed, at high doses there appears to be an increase in vomiting and reduction in latency. It was confirmed that neither M6 nor M16 had emetic activity in their own right. These data further emphasise the differences noted in the pharmacological effects of THC and CBD, which have been investigated by the applicant.

EXAMPLE 3

Growing of Medicinal *Cannabis*

Plants are grown as clones from germinated seeds, under glass at a temperature of 25° C.±1.5° C. for 3 weeks in 24-hour daylight; this keeps the plants in a vegetative state. Flowering is induced by exposure to 12 hour day length for 8-9 weeks.

No artificial pesticides, herbicides, insecticides or fumigants are used. Plants are grown organically, with biological control of insect pests.

The essential steps in production from seed accession to dried Medicinal *Cannabis* are summarised as follows:

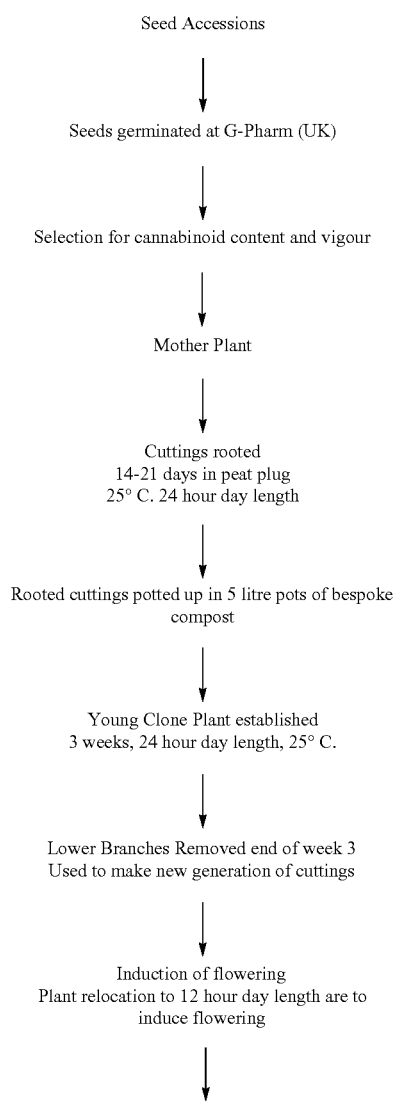

-continued

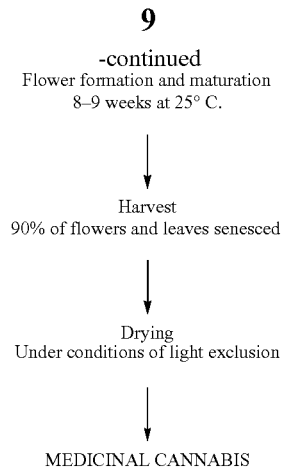

Flower formation and maturation
8–9 weeks at 25° C.

↓

Harvest
90% of flowers and leaves senesced

↓

Drying
Under conditions of light exclusion

↓

MEDICINAL CANNABIS

EXAMPLE 4

Determination of Cannabinoid Content in Plants and Extracts

Identity by TLC
a) Materials and Methods
Equipment Application device capable of delivering an accurately controlled volume of solution i.e. 1 μl capillary pipette or micro litre syringe.
  TLC development tank with lid
  Hot air blower
  Silica gel G TLC plates (SIL N-HR/UV254), 200 μm layer with fluorescent indicator on polyester support.
  Dipping tank for visualisation reagent.

| Mobile phase | 80% petroleum ether 60:80/20% Diethyl ether. |
|---|---|
| Visualisation reagent | 0.1% w/v aqueous Fast Blue B (100 mg in 100 ml de-ionised water). An optional method is to scan at UV 254 and 365 nm. | b) Sample Preparation
  i) Herbal Raw Material
  Approximately 200 mg of finely ground, dried cannabis is weighed into a 10 ml volumetric flask. Make up to volume using methanol:chloroform (9:1) extraction solvent.
  Extract by ultrasound for 15 minutes. Decant supernatant and use directly for chromatography.
  ii) Herbal Drug Extract
  Approximately 50 mg of extract is weighed into a 25 ml volumetric flask. Make up to volume using methanol solvent. Shake vigorously to dissolve and then use directly for chromatography.
c) Standards
0.1 mg/ml delta-9-THC in methanol.
0.1 mg/ml CBD in methanol.
  The standard solutions are stored frozen at −20° C. between uses and are used for up to 12 months after initial preparation.
d) Test Solutions and Method
  Apply to points separated by a minimum of 10 mm.
  i) either 5 μl of herb extract or 1 μl of herbal extract solution as appropriate,
  ii) 10 μl of 0.1 mg/ml delta-9-THC in methanol standard solution,
  iii) 10 μl of 0.1 mg/ml CBD in methanol standard solution.
  Elute the TLC plate through a distance of 8 cm, then remove the plate. Allow solvent to evaporate from the plate and then repeat the elution for a second time (double development).
  The plate is briefly immersed in the Fast Blue B reagent until the characteristic red/orange colour of cannabinoids begins to develop. The plate is removed and allowed to dry under ambient conditions in the dark.
  A permanent record of the result is made either by reproduction of the image by digital scanner (preferred option) or by noting spot positions and colours on a tracing paper.
Assay THC, THCA, CBD, CBDA and CBN by HPLC
a) Materials and Methods

| Equipment: | HP 1100 HPLC with diode array detector and autosampler. The equipment is set up and operated in accordance with in-house standard operating procedures (SOPlab037) |
|---|---|
| HPLC column | Discovery C8 5 μm, 15 × 0.46 cm plus Kingsorb ODS2 precolumn 5 μm 3 × 0.46 cm. |
| Mobile Phase | Acetonotrile:methanol:0.25% aqueous acetic acid (16:7:6 by volume) |
| Column Operating Temperature | 25° C. |
| Flow Rate | 1.0 ml/min |
| Injection Volume | 10 μl |
| Run time | 25 mins |
| Detection | Neutral and acid cannabinoids 220 nm (band width 16 nm) Reference wavelength 400 nm/bandwidth 16 nm Slit 4 nm Acid cannabinoids are routinely monitored at 310 nm (band width 16 nm) for qualitative confirmatory and identification purposes only. |
| Data capture | HP Chemistation with Version A7.01 software | b) Sample Preparation
  Approximately 40 mg of Cannabis Based Medicinal Extract is dissolved in 25 ml methanol and this solution is diluted to 1 to 10 in methanol. This dilution is used for chromatography.
  0.5 ml of the fill solution, contained within the Pump Action Sublingual Spray unit, is sampled by glass pipette. The solution is diluted into a 25 ml flask and made to the mark with methanol. 200 μl of this solution is diluted with 800 μl of methanol.
  Herb or resin samples are prepared by taking a 100 mg sample and treating this with 5 or 10 ml of Methanol/Chloroform (9/1 w/v). The dispersion is sonicated in a sealed tube for 10 minutes, allowed to cool and an aliquot is centrifuged and suitably diluted with methanol prior to chromatography.
c) Standards
  External standardisation is used for this method. Dilution of stock standards of THC, CBD and CBN in methanol or ethanol are made to give final working standards of approximately accurately 0.1 mg/ml. The working standards are stored at −20° C. and are used for up to 12 months after initial preparation.
  Injection of each standard is made in triplicate prior to the injection of any test solution. At suitable intervals during the processing of test solutions, repeat injections of standards are made. In the absence of reliable CBDA and THCA standards, these compounds are analysed using respectively the CBD and THC standard response factors.

The elution order has been determined as CBD, CBDA, CBN, THC and THCA. Other cannabinoids are detected using this method and may be identified and determined as necessary.

d) Test Solutions

Diluted test solutions are made up in methanol and should contain analytes in the linear working range of 0.02-0.2 mg/ml.

e) Chromatography Acceptance Criteria:

The following acceptance criteria are applied to the results of each sequence as they have been found to result in adequate resolution of all analytes (including the two most closely eluting analytes CBD and CBDA)

i) Retention time windows for each analyte:
      CBD 5.4-5.9 minutes
      CBN 7.9-8.7 minutes
      THC 9.6-10.6 minutes
   ii) Peak shape (symmetry factor according to BP method)
      CBD<1.30
      CBN<1.25
      THC<1.35
   iii) A number of modifications to the standard method have been developed to deal with those samples which contain late eluting impurity peaks e.g. method CBD2A extends the run time to 50 minutes. All solutions should be clarified by centrifugation before being transferred into autosampler vials sealed with teflon faced septum seal and cap.
   iv) The precolumn is critical to the quality of the chromatography and should be changed when the back pressure rises above 71 bar and/or acceptance criteria regarding retention time and resolution, fall outside their specified limits.

f) Data Processing

Cannabinoids can be subdivided into neutral and acidic— the qualitative identification can be performed using the DAD dual wavelength mode. Acidic cannabinoids absorb strongly in the region of 220 nm-310 nm. Neutral cannabinoids only absorb strongly in the region of 220 nm.

Routinely, only the data recorded at 220 nm is used for quantitative analysis.

The DAD can also be set up to take UV spectral scans of each peak, which can then be stored in a spectral library and used for identification purposes.

Data processing for quantitation utilises batch processing software on the Hewlett Packard Chemstation.

a) Sample Chromatograms

HPLC sample chromatograms for THC and CBD Herbal Drug extracts are provided in the accompanying Figures.

EXAMPLE 5

Preparation of the Herbal Drug Extract

A flow chart showing the process of manufacture of extract from the High-THC and High-CBD (non acid and acid forms) chemovars is given below:

Medicinal Cannabis (High-THC or High CBD)

↓

Chopping to predominantly 2 to 3 mm

↓

Optional decarboxylation step:
Heating at 100 to 150° C. for sufficient time to decarboxylate acid form of cannabiniods to produce neutral cannabinoids

↓

Extraction with a specified volume of liquid carbon dioxide over 6 to 8 hours

↓

Removal of $CO_2$ by depressurisation to recover crude extract

↓

"Winterisation"-Dissolution of crude extract in ethanol Ph. Eur. followed by chilling solution (-20° C./48 hrs) to precipitate unwanted waxes

↓

Removal of unwanted waxy material by cold filtration

↓

Removal of ethanol from the filtrate by thin film evaporation under reduced pressure

EXAMPLE 6

High CBD cannabis was grown under glass at a mean temperature of 21+2° C., RH 50-60%. Herb was harvested and dried at ambient room temperature at a RH of 40-45% in the dark. When dry, the leaf and flower head were stripped from stem and this dried biomass is referred to as "medicinal *cannabis*".

Medicinal *cannabis* was reduced to a coarse powder (particles passing through a 3 mm mesh) and packed into the chamber of a Supercritical Fluid Extractor. Packing density was 0.3 and liquid carbon dioxide at a pressure of 600 bar was passed through the mass at a temperature of 35° C. Supercritical extraction is carried out for 4 hours and the extract was recovered by stepwise decompression into a collection vessel. The resulting green-brown oily resinous extract is further purified. When dissolved in ethanol BP (2 parts) and subjected to a temperature of −20° C. for 24 hours a deposit (consisting of fat-soluble, waxy material) was thrown out of solution and was removed by filtration. Solvent was removed at low pressure in a rotary evaporator. The resulting extract is a soft extract which contains approximately 60% CBD with up to 4% tetrahydrocannabinol, within a total of other cannabinoids of 6%. Extracts were made using THCV and CBDV chemovars using the general method described above.

A high THC chemovar was similarly treated and yielded an extract containing approximately 60% THC and approximately 6% of other cannabinoids of which 1-2% is cannabidiol and the remainder is minor cannabinoids including cannabinol. Quantitative yield was 9% w/w based on weight of dry medicinal *cannabis*.

A person skilled in the art will appreciate that other combinations of temperature and pressure (in the range +10° C. to 35° C. and 60-600 bar) can be used to prepare extracts under supercritical and subcritical conditions.

EXAMPLE 7

Preparation of CBDA

Summary of Process:

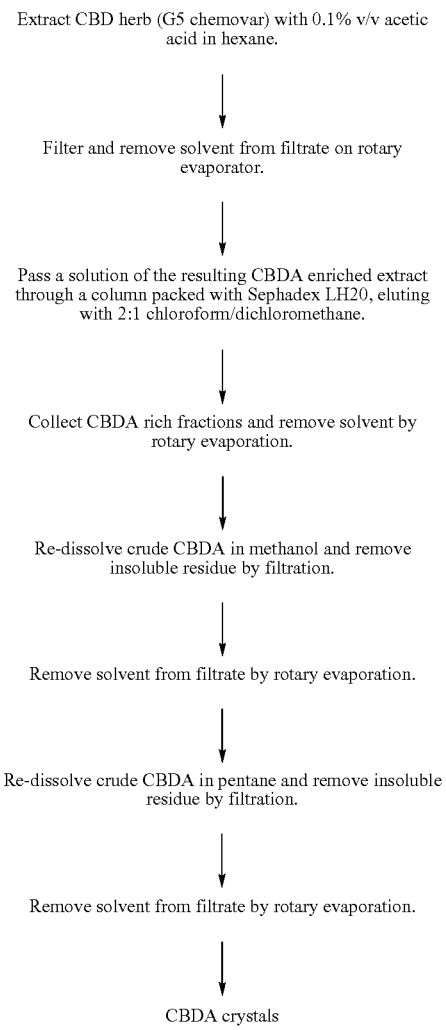

Yield:
100 g of G5 chemovar yields approx 5 g of purified CBDA.
Characteristics:
Pale yellow crystalline solid
Melting Point=45-48° C.
Chromatographic purity=94% CBDA by area normalisation
*CBD 3%.
THCA non detected i.e. <0.1%
THC non detected i.e. <0.1%
Material slowly decarboxylates in solution CBDA→CBD+CO$_2$
* As CBDA does not co-elute with CBD during processing of the extract in the low pressure column chromatography method employed, the detected CBD is likely to be formed from the breakdown of the CBDA during processing and analysis. This undesirable decarboxylation of the purified material might be minimised by manipulation of CBDA at sub-ambient temperatures.

EXAMPLE 8

Purification of CBD

Overview of Process

Starting from freshly harvested plant material the process comprises drying and decarboxylation of the plant material, optional treatment (e.g. milling) of the dried plant material to reduce the particle size (preferably to less than 2000 μm), extraction with liquid carbon dioxide, ethanolic precipitation to reduce the amount of non-target material, clean-up of the crude ethanolic extract by passage through activated charcoal, removal of solvent (ethanol) to produce a CBD-enriched fraction, and re-crystallisation of CBD from pentane.

Plant Material

GW Pharma Ltd has developed distinct varieties of *Cannabis* plant hybrids to maximise the output of the specific chemical constituents, cannabinoids. A "high CBD" chemovar designated G5 produces >90% total cannabinoid content as CBD (naturally occurring in the plant in the form of CBDA). Alternative "high CBD" varieties can be obtained—see for example, Common cannabinoids phenotypes in 350 stocks of *cannabis, Small and Beckstead, Lloydia vol* 36b, 1973, p 144-156—and bred using techniques well known to the skilled man to maximise cannabinoid content.

Solvents

All solvents used in the isolation and analysis of CBD (e.g., n-pentane) were, unless otherwise stated, of chromatographic or A.R. grade.

Standards

Reference materials from Sigma were used as standards in the analysis of extracts, intermediates and finished products, these were: $\Delta^9$ THC in methanol BN 10601/B (ca. 1 mg/ml) and CBD in methanol BN 10601/C (ca. 1 mg/ml).

Preparation of a Cannabidiol-Containing Extract

A cannabidiol-containing extract is prepared from a "high CBD" cannabis chemovar according to the following process:

Prepare ethanolic solution of botanical drug substance as follows:

harvest cannabis plant material, dry, reduce particle size by milling to less than 2000 μm

↓ decarboxylate milled plant material by heating to approximately 105° C. for 15 minutes, followed by approximately 145° C. for minimum of 55 minutes (NB decarboxylation time and temperature may be varied)

↓ extract with liquid carbon dioxide (CO$_2$) [Food Grade] for up to 10 hours Conditions: Approximately 60 bar ± 10 bar pressure and 10° C. ± 5° C.

↓

-continued

Removal of $CO_2$ by depressurisation to recover crude extract

↓

"Winterisation"-Dissolution of crude extract in ethanol followed by chilling solution (-20° C. ± 5° C./up to 52 hours) to precipitate unwanted waxes

↓

Removal of unwanted waxy material by cold filtration (20 mm filter)

↓ ethanolic solution of BDS (Stored at -20° C. ± 5° C.)

Extraction using liquid $CO_2$ is carried out under sub-critical conditions at a temperature of approximately 10° C.±5° C. using a pressure of approximately 60 bar±10 bar. Decarboxylated plant material is packed into a single column and exposed to liquid $CO_2$ under pressure for approximately 8 hours, $CO_2$ mass flow 1250 kg/hr±20%.

Following depressurisation and venting off of the $CO_2$ the crude BDS extract is collected into sealed vessels. The crude BDS extract is held at −20° C.±5° C.

The crude BDS extract contains waxes and long chain molecules. Removal is by "winterisation", whereby the crude BDS extract is warmed to e.g. 40° C.±4° C. to liquefy the material. Ethanol is added in the ratio of 2:1 ethanol volume to weight of crude BDS extract. The ethanolic solution is then cooled to −20° C.±5° C. and held at this temperature for approximately 48 hours.

On completion of the winterisation the precipitate is removed by cold filtration through a 20 μm filter, to give an ethanolic solution of the BDS.

Preliminary charcoal clean-up may be carried out by passing the ethanolic BDS solution (400-500 mg/ml) through a disposable plastic column (130 mm×27 mm i.d) packed with activated charcoal (decolourcarb DCL GDC grade, from Sutcliffe Speakman Carbons, 15.4 g per unit). Absolute ethanol B.P. (Hayman) is used as the solvent.

Ethanol and any water that may be present are removed by rotary evaporation or thin film evaporation under reduced pressure (60° C.±2° C., with vapour at 40° C.±2° C./172 mbar and 72 mbar±4 mbar) to produce a CBD-rich extract.

Solvent Re-Crystallisation

The CBD-rich extract is re-dissolving in a suitable solvent (e.g. n-pentane) and filtered to remove insoluble material. Solvent is them then removed, e.g. by rotary evaporation, to produce crystalline CBD. All steps are carried out according to standard laboratory procedures, such as would be known to those skilled in the art.

Product Characteristics

Yield:

3 g of CBD BDS yields approx 1 g of purified CBD.

Characteristics:

White crystalline solid.

Chromatographic purity>99% CBD by area normalization.

Chromatographic purity superior to commercially available CBD Sigma standard (refer to FIGS. 1 and 3).

THC non detected i.e. <0.1%

CBN non detected i.e. <0.1%

Identity confirmed by HPLC, GC and TLC retention behaviour compared to CBD Sigma standard.

Assay vs both Sigma CBD std in range 98.0-102.0%

Melting Point=64-66° C. (literature value=66-67° C.).

HPLC Analysis

The composition of the isolated products may be determined by HPLC analysis.

A typical HPLC assay for $\Delta^9$ THC, $\Delta^9$ THCA, CBD, CBDA and CBN may be carried out as follows:

a) Materials and Methods

| Chromatography Equipment and conditions: | |
|---|---|
| Equipment | Agilent (HP)1100 HPLC system with variable wavelength UV detector or diode array detector. |
| HPLC Column | Discovery C8 5 μm 15 cm × 0.46 cm |
| Pre-Column | Kingsorb C18 5 μm 3 cm × 0.46 cm |
| Mobile Phase | Acetonitrile:Methanol:0.25% w/v acetic acid (16:7:6 by volume) |
| Column Temp | 25° C. |
| Flow Rate | 1.0 ml min-1 |
| Detection | 220 nm 600 mA f.s.d. Second wavelength 310 nm |
| Injection Volume | 10 μl |
| Run Time | 20-25 minutes (may be extended for samples containing small amount of late-eluting peaks) |

Elution Order CBD, CBDA, $\Delta^9$ THCV, CBN, $\Delta^9$ THC, CBC, $\Delta^9$ THCA b) Sample Preparation Samples of "pure" cannabidiol are diluted in methanol prior to HPLC analysis. Optimal dilutions may be determined empirically.

Herbal *cannabis* samples are prepared by taking a 100 mg sample and treating this with 5 or 10 ml of Methanol/Chloroform (9/1 w/v). The dispersion is sonicated in a sealed tube for 10 minutes, allowed to cool and an aliquot is centrifuged and suitably diluted with methanol prior to chromatography.

c) Standards

Stock standard solutions of CBD, CBN and $\Delta^9$ THC in methanol at approximately 1 mg $ml^1$ are stored at −20° C. Diluted working standards (0.1 mg/ml for $\Delta^9$ THC and CBD and 0.01 mg/ml for CBN) are prepared in methanol from the stock standards and stored at −20° C. (maximum period of twelve months after initial preparation). After preparation, standard solutions must be aliquoted into vials to reduce the amount of standard exposed to room temperature. Prior to use in an HPLC sample assay, the required number of standard vials are removed and allowed to equilibrate to room temperature.

Injection of each standard is made in triplicate prior to the injection of any test solution. At suitable intervals during the processing of test solutions, repeat injections of standards are made. In the absence of reliable CBDA and $\Delta^9$ THCA standards, these compounds are analysed using respectively the CBD and $\Delta^9$ THC standard response factors.

d) Test Solutions

Diluted test solutions are made up in methanol and should contain analytes in the linear working range of 0.02-0.2 mg/ml.

e) Chromatography Acceptance Criteria:

The following acceptance criteria are applied to the results of each sequence as they have been found to result in adequate resolution of all analytes (including the two most closely eluting analytes CBD and CBDA)

TABLE 1

Retention time windows and Relative Retention Time (RRT) to $\Delta^9$ THC for each analyte

| Cannabinoid | Retention time (minutes) | RRT (THC) |
|---|---|---|
| CBD | 5.1-5.8 | 0.58 |
| CBN | 7.4-8.3 | 0.83 |
| $\Delta^9$ THC | 9.0-10.0 | 1.00 |
| CBDA | 5.5-6.2 | 0.615 |
| $\Delta^9$ THCV | 5.9-6.2 | 0.645 |
| CBC | 11.6-12.8 | 1.30 |
| $\Delta^9$ THCA | 14.6-16.0 | 1.605 |

TABLE 2

Peak Shape (Symmetry Factor according to British Pharmacopoeia method)

| Cannabinoid | Symmetry factor |
|---|---|
| CBD | <1.30 |
| CBN | <1.25 |
| $\Delta^9$ THC | <1.35 | f) Data Processing

Cannabinoids can be subdivided into neutral and acidic—the qualitative identification can be performed using the DAD dual wavelength mode. Acidic cannabinoids absorb strongly in the region of 220 nm-310 nm. Neutral cannabinoids only absorb strongly in the region of 220 nm.

Routinely, only the data recorded at 220 nm is used for quantitative analysis.

The DAD can also be set up to take UV spectral scans of each peak, which can then be stored in a spectral library and used for identification purposes.

Data processing for quantitation utilises batch processing software on the Hewlett Packard Chemstation.

g) Calculation:

Chromatographic purity of cannabinoid samples is calculated as a % of total cannabinoid content by area normalization.

Capillary Gas Chromatography (GC) Analysis a) Chromatography Equipment and Conditions

| Equipment | Agilent (HP) 5890 or 6890 GLC system with HP7673 Autosampler and FID detector |
|---|---|
| GLC column | SE54(EC5) 30 m × 0.32 mm i.d. (Alltech) phase thickness 0.25 μm |
| Flow rate | Constant pressure (10.3 psi). Normal initial flow rate 34 cm sec$^{-1}$ (2.0 ml min$^{-1}$) |
| Column oven | 70° C. initially then ramp 5° C. min$^{-1}$ to 250° C. Hold at 250° C. for 15 minutes. |
| Injector temp | 250° C. |
| Detector temp | 325° C. |
| Injection Vol | 1 μl, split ratio 2.5:1 |
| Run time | 45 minutes |
| Fuel gases | Hydrogen 40 ml min$^{-1}$ Air 450 ml min$^{-1}$ Helium 45 ml min$^{-1}$ | b) Standard Preparation

Stock standard solutions of CBD, CBN and $\Delta^9$ THC in methanol at approximately 1 mg ml$^{-1}$ are stored at −20° C. Diluted working standards (0.1 mg/ml for $\Delta^9$ THC and CBD and 0.01 mg/ml for CBN) are prepared in methanol from the stock standards and stored at −20° C. (maximum period of twelve months after initial preparation). Allow an aliquot pipetted into an autosampler vial to equilibrate to room temperature prior to use in a GC assay.

c) Sample Preparation

Samples of final products, i.e. "pure" cannabidiol, are diluted in methanol prior to HPLC analysis. Optimal dilutions may be determined empirically.

*Cannabis* plant material samples are prepared by taking 100 mg chopped dried material and treating this with 5 or 10 ml of Methanol/Chloroform (9:1 v/v). Extract the sample in an ultrasonic bath for 15 minutes and allow to stand in the dark for 18 hours.

d) Chromatography Procedure

Standard solutions are used to provide quantitative and retention time data. These can be typically injected in triplicate prior to the injection of any sample solutions and then singularly at suitable intervals during the run, with a maximum of 10 test samples in between standards.

TABLE 3

| Retention times | |
|---|---|
| THCV | 33.7-34.5 minutes |
| CBD | 35.6-36.3 minutes |
| $\Delta^9$ THC | 37.2-38.1 minutes |
| CBN | 38.5-39.1 minutes |

TLC Analysis

The qualitative composition of final products and starting materials may also be monitored by TLC.

TLC uses both retention time and characteristic spot colour to effectively identify the cannabinoid/cannabinoid acid components in a complex mixture. Methanolic solutions of the final products and starting material, plus standards, are prepared for TLC. An aliquot is spotted-onto a TLC plate, alongside suitable reference samples (e.g. for at least $\Delta^9$ THC and CBD). Following exposure to Fast Blue B reagent, THC and THCA present as pink spots, while CBD and CBDA are orange in colour. Neutrals can be distinguished from the acids by comparison of the Rf value to that obtained for the standards. Identity is confirmed by comparison of Rf and colour of the sample spot, to that obtained for the appropriate standard.

A typical TLC protocol is as follows:

a) Materials and Methods

Equipment:

Application-device capable of delivering an accurately controlled volume of solution i.e. 1 μl capillary pipette or micro litre syringe.

TLC development tank with lid

Hot air blower

Silica gel G TLC plates (SIL N-HR/UV254), 200 μm layer with fluorescent indicator on polyester support.

Dipping tank for visualisation reagent.

| Mobile phase | 80% petroleum ether 60:80/20% Diethyl ether. |
|---|---|
| Visualisation reagent | 0.1% w/v aqueous Fast Blue B salt BN (Sigma Corp) (100 mg in 100 ml de-ionised water). An optional method is to scan at UV 254 and 365 nm. | b) Sample Preparation
i) Herbal Raw Material

Approximately 200 mg of finely ground, dried cannabis is weighed into a 10 ml volumetric flask. Make up to volume using methanol:chloroform (9:1) extraction solvent.

Extract by ultrasound for 15 minutes. Decant supernatant and use directly for chromatography.

ii) Final Products

The final products (crystalline CBD) are dissolved in methanol to a suitable concentration (which may be determined empirically) then used directly for chromatography. All sample preparations should produce a final concentration of about 0.5 mg/ml.

iii) Botanical Drug Substance

Accurately weigh approximately 50 mg of botanical drug substance into a 25 ml volumetric flask. Dissolve to make volume with HPLC grade methanol.

c) Standards 0.1 mg/ml $\Delta^9$-THC in methanol (Sigma).
0.1 mg/ml CBD in methanol (Sigma).

The standard solutions are stored frozen at −20° C. between uses and are used for up to 12 months after initial preparation.

d) Test Solutions and Method

Apply to points separated by a minimum of 10 mm.
i) either 5 μl of herb extract or 1 μl of pure cannabinoid/enriched extract solution or 1 μl of diluted column eluate as appropriate,
ii) 5 μl of 0.1 mg/ml $\Delta^9$-THC in methanol standard solution,
iii) 5 μl of 0.1 mg/ml CBD in methanol standard solution.

Dry the prepared plate with a hot air blower.

Place the base of the TLC plate in a development tank containing the mobile phase and saturated with vapour.

Elute the TLC plate through a distance of 8 cm, then remove the plate. Allow solvent to evaporate from the plate and then repeat the elution for a second time (double development). Remove plate and allow it to dry in air.

The entire plate is briefly immersed in the Fast Blue B reagent until the characteristic red/orange colour of cannabinoids begins to develop. The plate is removed and allowed to dry under ambient conditions in the dark.

| Cannabinoids will give an orange-purple colour: | | |
|---|---|---|
| Cannabidiol | CBD | orange (fastest running) |
| $\Delta^9$ Tetrahydrocannabinol | THC | pink |
| Cannabinol | CBN | purple |
| Cannabichromene | CBC | pink purple |
| Cannabigerol | CBG | orange |
| $\Delta^9$ tetrahydrocannabivarin | THCV | purple |

The corresponding acids form streaks of the same colour as the neutral component spots. The acids run at lower $R_f$.

The invention claimed is:

1. A method of treating motion sickness in a mammal comprising administering a pharmaceutically acceptable amount of, or an extract consisting essentially of a pharmaceutically acceptable amount of, CBD and/or CBDA and/or the propyl variants CBDV and/or CBDVA, wherein the amount of CBD and/or CBDA and/or the propyl variants CBDV and/or CBDVA is greater than 50% of the total cannabinoid content, wherein the CBDA, and/or CBDVA and/or CBD and/or CBDV is/are present as a *cannabis* extract, and wherein the *cannabis* extract contains less than 10% (w/w) of other cannabinoids.

2. A method as claimed in claim 1, wherein the *cannabis* extract contains less than 5% (w/w) of other cannabinoids.

3. A method as claimed in claim 1, wherein the *cannabis* extract contains less than 2% (w/w) of other cannabinoids.

4. A method as claimed in claim 1, wherein the other cannabinoids include THC or THCV.

5. A method as claimed in claim 1, wherein the CBDA and/or CBDVA and/or CBD and/or CBDV is CBDA.

6. A method as claimed in claim 1, wherein the CBDA and/or CBDVA and/or CBD and/or CBDV is CBDVA.

7. A method as claimed in claim 1, wherein the CBDA and/or CBDVA and/or CBD and/or CBDV is CBD.

8. A method as claimed in claim 1, wherein the CBDA and/or CBDVA and/or CBD and/or CBDV is CBDV.

9. A method as claimed in claim 1, wherein the *cannabis* extract comprises 0.1-2% (w/w) of THC and/or THCA.

10. A method of treating motion sickness in a mammal comprising administering a *cannabis* extract consisting essentially of a pharmaceutically acceptable amount of CBD and/or CBDA and/or the propyl variants CBDV and/or CBDVA, wherein the *cannabis* extract comprises greater than 2% (w/w) of CBDA and/or CBDVA and/or CBD and/or CBDV, and wherein the *cannabis* extract contains less than 10% (w/w) of other cannabinoids.

11. A method as claimed in claim 10, wherein the *cannabis* extract comprises greater than 5% (w/w) of CBDA and/or CBDVA and/or CBD and/or CBDV.

12. A method as claimed in claim 10, wherein the *cannabis* extract comprises greater than 7% (w/w) of CBDA and/or CBDVA and/or CBD and/or CBDV.

13. A method as claimed in claim 10, wherein the CBDA and/or CBDVA and/or CBD and/or CBDV is CBDA.

14. A method as claimed in claim 10, wherein the CBDA and/or CBDVA and/or CBD and/or CBDV is CBDVA.

15. A method as claimed in claim 10, wherein the CBDA and/or CBDVA and/or CBD and/or CBDV is CBD.

16. A method as claimed in claim 10, wherein the CBDA and/or CBDVA and/or CBD and/or CBDV is CBDV.

* * * * *